(12) United States Patent
Khan et al.

(10) Patent No.: US 10,130,482 B2
(45) Date of Patent: Nov. 20, 2018

(54) FLEXIBLE PROSTHETIC BEARING FOR JOINT

(71) Applicant: Biomet UK Limited, Bridgend (GB)

(72) Inventors: Mohammed Imran Khan, Berkshire (GB); Russell Lloyd, Swindon (GB); David Wycliffe Murray, Oxford (GB); Christopher Dodd, Oxford (GB); John O'Connor, Oxfordshire (GB)

(73) Assignee: Biomet UK Limited, Bridgend Smith Glamorgan (GB)

( * ) Notice: Subject to any disclaimer, the term of this patent is extended or adjusted under 35 U.S.C. 154(b) by 0 days.

(21) Appl. No.: 15/116,447

(22) PCT Filed: Dec. 8, 2014

(86) PCT No.: PCT/GB2014/053634
§ 371 (c)(1),
(2) Date: Aug. 3, 2016

(87) PCT Pub. No.: WO2015/118287
PCT Pub. Date: Aug. 13, 2015

(65) Prior Publication Data
US 2017/0007411 A1      Jan. 12, 2017

(30) Foreign Application Priority Data

Feb. 5, 2014  (GB) .................................. 1401991.3

(51) Int. Cl.
*A61F 2/38*       (2006.01)
*A61F 2/30*       (2006.01)

(52) U.S. Cl.
CPC .......... *A61F 2/389* (2013.01); *A61F 2/30965* (2013.01); *A61F 2/3872* (2013.01);
(Continued)

(58) Field of Classification Search
CPC ................ A61F 2/3872; A61F 2/30756; A61F 2/30965; A61F 2002/3004;
(Continued)

(56) References Cited

U.S. PATENT DOCUMENTS 4,919,667 A    4/1990   Richmond
5,171,322 A    12/1992  Kenny
(Continued)

FOREIGN PATENT DOCUMENTS

CN    103007356 A    4/2013
CN    106456333 A    2/2017
(Continued)

OTHER PUBLICATIONS

"European Application Serial No. 14828496.1, Response filed May 3, 2017 to Action dated Oct. 21, 2016", 11 pgs.
(Continued)

*Primary Examiner* — Brian Dukert
(74) *Attorney, Agent, or Firm* — Schwegman Lundberg & Woessner, P.A.

(57) ABSTRACT

A bearing for a total or partial joint replacement prosthesis: the bearing having a body and a reinforcing element which strengthens the bearing and which forms an attachment member, and/or the bearing being formed at least partially from polymeric or composite material the bearing comprising a lower modulus portion and a higher modulus portion, one portion of the bearing being at least partially encased by the other portion of the bearing. Also provided is a method for of forming the bearing, and a total or partial joint replacement prosthesis comprising the hearing.

19 Claims, 2 Drawing Sheets

(52) U.S. Cl.
CPC ........... *A61F 2002/30014* (2013.01); *A61F 2002/3038* (2013.01); *A61F 2002/30481* (2013.01); *A61F 2002/30576* (2013.01); *A61F 2002/30919* (2013.01); *A61F 2240/002* (2013.01)

(58) Field of Classification Search
CPC .. A61F 2002/30131; A61F 2002/30014; A61F 2002/3038
See application file for complete search history.

(56) References Cited

U.S. PATENT DOCUMENTS 8,192,491 B2 * 6/2012 Fox ..................... A61F 2/3872
623/14.12
2008/0255665 A1 10/2008 Weissberg

FOREIGN PATENT DOCUMENTS

| WO | WO-2006097932 | A2 | 9/2006 | |
|----|----|----|----|----|
| WO | WO-2012106763 | A1 | 8/2012 | |
| WO | WO 2012168715 | A1 * | 12/2012 | ........... A61F 2/3872 |
| WO | WO-2012168715 | A1 | 12/2012 | |
| WO | WO-2015118287 | A1 | 8/2015 | |

OTHER PUBLICATIONS

"International Application Serial No. PCT/GB2014/053634, International Search Report dated Mar. 20, 2015", 3 pgs.
"International Application Serial No. PCT/GB2014/053634, Written Opinion dated Mar. 20, 2015", 5 pgs.
"Chinese Application Serial No. 201480077048.0, Office Action dated Oct. 9, 2017", w/English Translation, 14 pgs.
"Chinese Application Serial No. 201480077048.0, Response filed Feb. 2, 2018 to Office Action dated Oct. 9, 2017", w/translated claims, 11 pgs.

* cited by examiner

FLEXIBLE PROSTHETIC BEARING FOR JOINT

CLAIM OF PRIORITY

This application is a U.S. National Stage Filing under 35 U.S.C. 371 from International Application No. PCT/GB2014/053634, filed on 8 Dec. 2014, and published as WO 2015/118287 A1 on 13 Aug. 2015, which claims the benefit to United Kingdom Application No. 1401991.3, filed on 5 Feb. 2014 the benefit of priority of each of which is claimed hereby, and each of which are incorporated by reference herein in its entirety.

The invention relates to an at least partially flexible bearing for a prosthetic or natural joint. The bearing may achieve fully comment contact throughout the full range of joint movement, and may be anatomically shaped.

BACKGROUND

Existing prosthetic joint bearings are often configured to maintain congruent contact with the hones or prosthetics forming the joint throughout the range of joint movement.

In order to maintain congruent contact, it is often necessary for the bearings to take a non-anatomical shape. This is because previous anatomically shaped prosthetic bearings have not been suitable for maintaining congruent contact throughout the range of joint movement, as they are not able to mimic the natural flexibility of cartilage white remaining rigid enough to support the joint adequately.

An aim of the present invention is to allow the use of anatomical components and a congruent bearing in a low wear bearing combination. The bearing may achieve fully congruent contact throughout the full range of flexion, extension and rotation of a joint. In the case of a bearing for use in a knee prosthesis, the bearing is suitable for use with an anatomical (poly-radial, poly-centric) femoral component or a spherical femoral component.

The bearing maintains the low wear and extended range of movement associated with a fully congruent bearing design but allows the use of anatomical femoral and tibial surfaces. In addition, due to the material properties of the bearing, this design offers: shock absorbance, increased longevity, increased intraoperative flexibility, unique patient fit and placement, improved kinematics, ability to be used on young active patients and ease of revision. Further, it may be possible to use thinner components to allow increased bone conservation.

Also, it is an aim of the invention to allow the use of prosthetics wherein more of the natural joint is retained. For example, if the bearing is used in a prosthetic knee replacement (unicompartmental or otherwise), it may be possible to retain the natural condyles on the femur and/or tibia for use with the bearing. Only condyles which actually require replacement would have to be replaced. An improved bearing which allows more of the natural tissue to be retained has obvious benefits for the patient. Further, as the tearing is typically more flexible than existing bearings, it can be inserted or replaced using a smaller incision, which is less traumatic for a patient.

STATEMENT OF INVENTION

An embodiment of the present invention provides a bearing for a total or partial joint replacement prosthesis, the bearing having a body and a reinforcing element which strengthens the bearing and which forms an attachment member.

Also provided is a method of forming the bearing. The method may comprise, for example: over-moulding the body over the reinforcing element; dip casting the body over the reinforcing element; reaction injection moulding the body into the reinforcing element; structural reaction injection moulding the body from a polymeric or composite mixture, or forming the body and then drilling or engraving channels in the body into which the reinforcing element is then inserted or formed.

The reinforcing element may be partially within the body, and extend out of the body to form the attachment member.

The reinforcing element may comprise a fibre.

The reinforcing element may comprise a plurality of fibres.

The fibres may be woven together to form the attachment member.

The fibres may be moulded or adhered together to form the attachment member.

The attachment member may comprise a loop.

The attachment member may be configured to be attached to a prosthesis.

The attachment member may be configured to be attached to a clip.

The attachment member may be configured to be attached to bone or soft tissue.

The bearing may comprise a plurality of attachment members.

The fibre may form a mesh which permeates the body.

The fibre may form a mesh which substantially encases the body.

The joint replacement prosthesis may be a knee joint replacement prosthesis and the attachment member may be adapted for attachment to a tibial wall.

The bearing may further comprise a lower modulus portion and a higher modulus portion, one modulus portion of the bearing being at least partially encased by the other modulus portion of the bearing.

A core portion of the bearing may be formed from lower modulus material than an outer portion of the bearing.

The method of forming a bearing, when the body further comprises a lower modulus portion and a higher modulus portion, may comprise forming the lower modulus portion within the higher modulus portion, or forming the higher modulus portion onto the lower modulus portion.

A further embodiment of the present invention provides a bearing for a total or partial joint replacement prosthesis, the bearing being formed at least partially from polymeric or composite material, the bearing comprising a lower modulus portion and a higher modulus portion, one portion of the bearing being at least partially encased by the other portion of the bearing. Also provided is a method of forming the bearing. The method may comprise, for example: over-moulding one portion over the other portion; dip casting one portion over the other portion; reaction injection moulding one portion into the other portion; or structural reaction infection moulding the bearing from a polymeric or composite mixture.

The polymeric or composite material may comprise low modulus polyurethane, polycarbonate, urethane, hydrogel, hydrogel reinforced with circumferential fibres, high density polyethylene, ultra-high-molecular-weight polyethylene, polyether ether ketone, carbon-fibre reinforced polyether ether ketone, other polyaryletherketones, other carbon-fibre reinforced polyaryletherketones or higher modulus polyurethanes.

The lower modulus portion may be at least partially encased by the higher modulus portion.

The lower modulus portion may be formed integrally with the higher modulus portion.

A core portion of the bearing may be formed from lower modulus material than an outer portion of the bearing.

The bearing may further comprise additional sections of differing moduli.

The moduli of the sections vary from the edge of the bearing to the centre.

The bearing may be substantially annular, or annular section shaped, or have a thin central section.

The reinforcing element may extend through the lower modulus portion and the higher modulus portion.

The bearing may be formed at least partially from flexible material.

The bearing may comprise a web section, wherein the web section may be a central section of the bearing.

Also provided is a total or partial joint replacement prosthesis comprising a bearing having any of the above features.

DESCRIPTION OF FIGURES

The invention will now be further described, by way of example only, with reference to the following figures, in which.

DETAILED DESCRIPTION

Figure 1A:
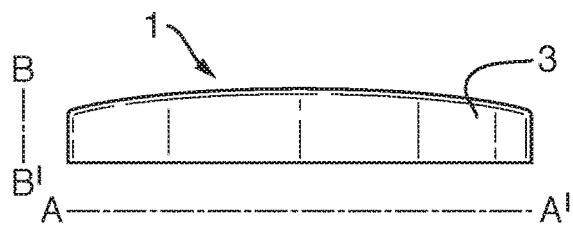
FIG. 1A is side view of an embodiment of the bearing.
Figure 1B:
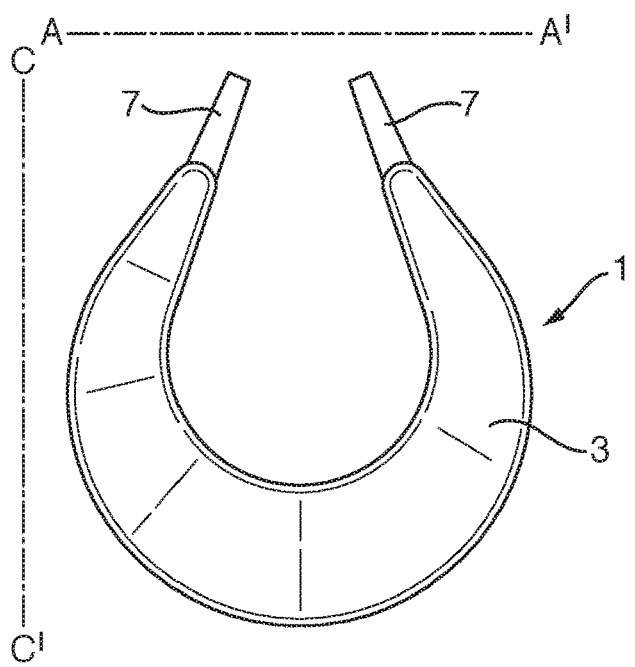
FIG. 1B is a plan view of art embodiment of the bearing.

The sagittal, coronal and horizontal planes are as shown in FIG. 1. With reference to FIG. 1A, line A-A' lies in the sagittal plane and line B-B' lies in the coronal plane. With reference to FIG. 1B line A-A' lies in the sagittal plane and line C-C' lies in the horizontal plane. Lines A-A', B-B' and C-C' are mutually perpendicular.

Figure 2A:
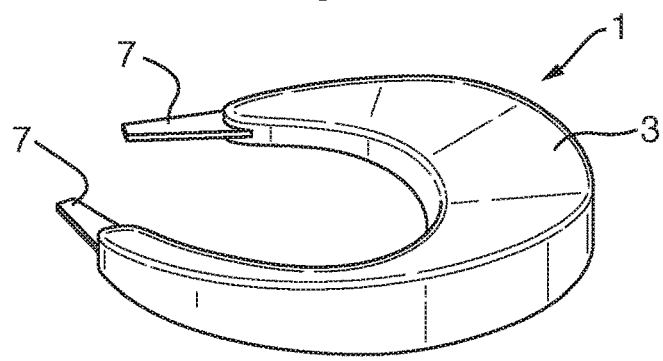
FIG. 2A is a perspective view of an embodiment of the bearing.
Figure 2B:
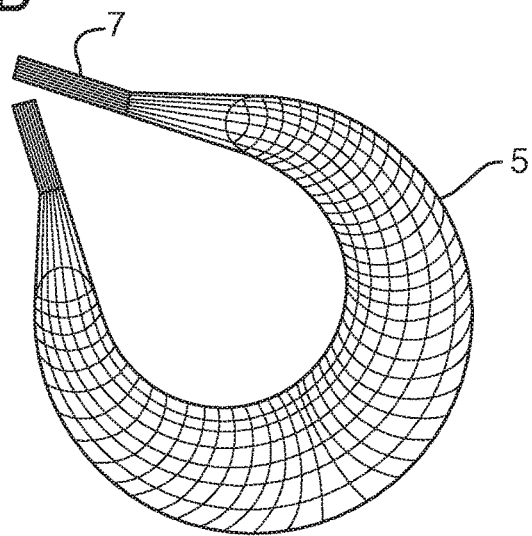
FIG. 2B is a plan view of a reinforcing element and attachment members of an embodiment of the bearing.

An embodiment of the invention provides a bearing 1 for use in a total or partial joint replacement prosthesis 11. FIG. 2A shows an exterior view of an embodiment of bearing 1, and FIG. 2B shows an arrangement of the reinforcing element 5 and the attachment member 7 only. The bearing 1 consists of a body 3 and a reinforcing element 5, wherein the reinforcing element 5 extends out of the body 3 of the bearing 1 to form an attachment member 7.

The body 3 of the bearing is shaped so as to provide support for the artificial and/or natural element of the joint into which it is to be inserted, ideally such that the bearing 1 is fully congruent with the condyles of the bones forming the joint (or prosthetics replacing the bones) throughout the natural range of movement of the joint. The exact dimensions of the bearing 1 are tailored to the joint into which the prosthesis 11 is being inserted. The dimensions of the bearing 1 may be varied in the sagittal, coronal or horizontal planes. In addition to tailoring the bearing 1 for the size of the joint, the bearing 1 may also be altered depending on expected load. For example, thicker bearings or bearings having a higher modulus may be used for comparatively heavy patients.

The bearing 1 may be configured for use in a total or partial knee replacement prosthesis 11. In this instance, the most favourable shape for the body 3 of the hearing 1 is a substantially horseshoe-shaped annular section (in the horizontal plane), as shown in FIG. 2A. This is because the bearing 1 is configured to partially or completely replace the meniscus in the knee, and to provide the support and shock absorption otherwise provided by the meniscus. In order to ensure that the femur (or femur replacing portion of a prosthetic) remains in the correct position relative to the bearing 1, the bearing 1 is configured to provide a concave surface into which the bottom of the femur (or femur replacing portion of a prosthetic) can sit. The bearing 1 may have a partially circumferential portion which is thicker than a central portion of the bearing 1 in order to provide the concave surface, as shown in FIG. 2A. That is, in the sagittal and coronal planes, the cross section of the bearing 1 forms a u-shaped curve.

Alternatively, the bearing could be configured for use in, for example, an ankle prosthesis, in which case the bearing would take a different anatomical shape.

In the case of a bearing 1 configured for implantation into the knee joint, if the central portion of the bearing 1 is configured to be thinner in the sagittal and coronal planes than the partially circumferential portion, the central portion may be formed from a solid element of the same material as the circumferential portion, or a different material, but having a thinner cross section (as shown in FIG. 2A). Alternatively, the central portion may be formed from a web of the same material as the circumferential portion (or a different material), rather than a solid element.

It is envisaged that the circumferential portion can provide the bulk of the support for the femur (or femur replacing portion of a prosthetic). The central portion solid element or web can be configured to simply provide support for the circumferential portion, holding the circumferential portion in the correct shape. If the support for the circumferential portion is not necessary, the central portion can be omitted, leaving a gap in the centre of the bearing 1. Alternatively, the bearing 1 may be configured such that the central portion provides substantial support directly for the femur (or femur replacing portion of a prosthetic).

Typically the base section of the bearing 1 is shaped so as to conform to the top surface of all or part of the tibia (or tibia replacing portion of a prosthetic). The top section of the tibia (or tibia replacing portion of a prosthetic) is typically substantially flat in the transverse plane, so the corresponding base surface of the bearing 1 is then also configured to present a substantially flat surface. Alternatively, depending on the exact shape of the tibia (or tibia replacing portion of a prosthetic) after surgery has been performed, the base surface may be configured to present a different corresponding shape as required.

The outer side portions of the bearing 1 parallel to the vertical axis are typically configured to be flat when not under load, such that the bearing 1 presents a substantially constant cross section around the outer portion parallel to the horizontal plane. This is illustrated in FIGS. 1A and 2A. However, the bearing 1 may alternatively present a slightly convex profile, such that the radius of the bearing 1 increases and then decreases as the vertical position varies.

The bearing 1 can be further configured such that the thickness of the body 3 is reduced with proximity to the attachment member 7 or members 7. That is, for an annular section shaped bearing 1, the bearing 1 can be thicker around the curve of the arch section, so as to afford support in the regions where it is most required around the outer lateral and medial portions of the knee joint. This is illustrated in FIGS. 1A, 1B and 2A.

The bearing 1 comprises a reinforcing element 5. The reinforcing element 5 may take the form of one or more elongate members, which may comprise fibres. The fibres may be individual cords (of single or multiple fibres), or woven into a mesh. The fibres may be connected together by knotting, or by moulding or adhering at connection points. The fibres may be adhered together using any suitable adhesive.

The fibres may substantially encase the body 3 of the bearing 1, or may alternatively permeate the body 3 of the bearing 1 and be partially or completely encased therein.

The reinforcing elements 5 may, alternatively, constitute a series of rigid or flexible struts or a solid rigid member within or around the body 3 of the bearing 1. Alternatively, one or more sheets of woven fibres could be used. The reinforcing element 5 may have a higher average modulus than the average modulus of the body 3 of the bearing 1.

The reinforcing elements 5 may form an attachment member 7, or a plurality of attachment members 7. In some configurations, the reinforcing elements 5 are formed from a fibre or a plurality of fibres, and the attachment members 7 are the sections of the fibres which protrude from the body 3 of the bearing 1. The protruding sections of the fibre or fibres which form an attachment member 7 may be the ends of the fibres, or the fibre may be looped so as to re-enter the body 3 of the bearing 1 with the attachment member 7 or attachment members 7 formed by the fibre loop. If a plurality of fibres are used, the fibres may be linked together to form a material clip 9, which acts as the attachment member 7, by knotting, moulding or adhering. The material clip 9 may also be encased within a further material, for example a high modulus polymer or metal.

In embodiments where the body 3 of the bearing 1 forms an annular section shape in the horizontal plane, and especially where the annular section shape is a substantially horseshoe shape, an attachment member 7 may protrude from both ends of the 'arms' of the horseshoe and be linked in the middle to form a loop. Alternatively, one or more attachment members 7 may protrude from either or both arms of the horseshoe as shown in FIGS. 1B, 2A and 2B.

Figure 3:
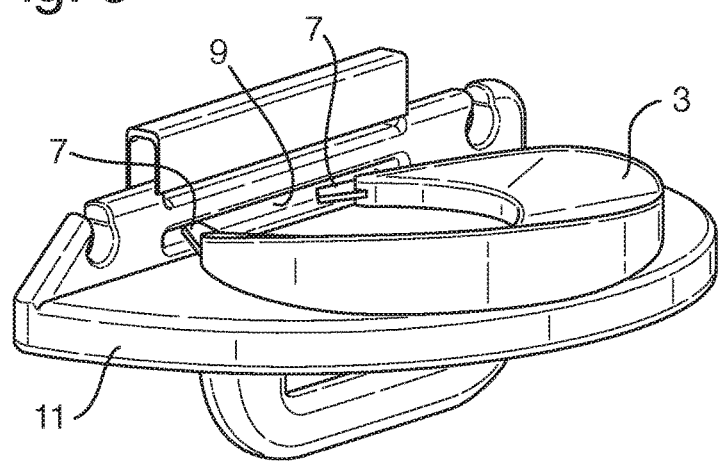
FIG. 3 is a perspective view of a prosthesis with an attached bearing.

The attachment member 7 may be configured to connect to the tibial wall (of either the tibia or a tibia replacing portion of a prosthetic), as shown in FIG. 3, where the attachment member connects to the tibia replacing portion of a prosthesis 11. The attachment member 7 may also or alternatively be configured to be tethered anteriorly and/or posteriorly to soft tissue via suturing of the reinforcing fibres or moulded members or by the use of bone or tethering anchors.

Further connection elements beyond the attachment member 7 may be used. For example, the bearing 1 element may be partially held in position by raised sections on either or both of the femur and tibia (or femur and tibia replacing portions of prosthetics. The ridges may be created by adding additional material to the bone or prosthesis 11, or by removing sections of the bone or prosthesis 11 to leave a raised section.

A prosthesis 11 may be used which is specifically configured to connect to the bearing 1, in particular, to the attachment member 7 or members 7. For example, a prosthesis 11 may be used which has a clip or slot 9 which corresponds to the attachment member 7 or members 7 of the bearing 1 and which is therefore designed to provide a reliable connection between the bearing 1 and the prosthesis 11, as shown in FIG. 3.

In addition to, or alternatively to, connecting to a prosthesis 11, the bearing 1 may be configured to be connected directly to another bearing 1. For example, in the case that the bearing 1 is configured to be used in a total or partial knee replacement prosthesis 11, a bearing 1 may be used to cushion the joint between the medial condyles of the femur and the tibia, and a further bearing 1 may be used to cushion the joint between the lateral condyles of the femur and the tibia. Of course, in this example, the condyles of the femur and the tibia may be fully or partially replaced by appropriate prostheses. The bearings may then be configured with appropriate connectors so as to connect directly to one another, in this way, the bearings can mutually support one another, reducing the possibility of either bearing 1 becoming dislodged. Alternatively, a larger bearing which cushions the joint area between the medial and lateral condyles of the femur and the tibia could be used.

If clips 9 are used in the attachment members 7, the clips 9 may attach onto the anterior edge of the tibial tray wall or through openings in, or on the sides of, the walls. The bearing 1 may also be attached to the centre of the tibial wall of the tibia (or tibia replacing portion of a prosthetic) for example by use of a bone or tethering anchor or a fibre loop/moulded member. Also, the fibres may be moulded Into a higher modulus material clip 9 that attaches to the tibial wall or is tethered anteriorly and/or posteriorly to soft tissue via suturing of the reinforcing fibres or moulded members or by the use of bone or tethering anchors. The bearing 1 may be attached to the femur, tibia, soft tissue or prosthesis 11, or any combination of these elements.

The components of the bearing 1 must all be suitable for implantation in a living body.

The body 3 of the bearing 1 may be manufactured from a flexible polymeric material such as low modulus polyurethane or polycarbonate urethane or hydrogel that may be reinforced with circumferential fibres to control the deformation and to minimise creep. Other materials such as, but not limited to, high density polyethylene (HOPE), ultra-high-molecular-weight polyethylene (UHMWPE), polyether ether ketone (PEEK), carbon-fibre reinforced polyether ether ketone (CFR-PEEK), other polyaryletherketones (PAEK), other carbon-fibre reinforced polyaryletherketones (CFR-PAEK) or higher modulus polyurethanes may also be used. The core of the bearing 1 may incorporate one or more polymer(s) that have different moduli to modify its deformation behaviour. The bearing 1 may also be constructed from a series of layers of material, either alternating layers or layers where each material is used once. The layers may be stacked along one or more of the vertical, sagittal and coronal axes, or may form concentric layers.

The attachment members 7 and clips 9 may be manufactured from implantable polymers. In some embodiments of the invention, the implantable polymers have a Young's modulus (E) of 300 MPa or greater. In other embodiment, the implantable polymers have a Young's modulus of 800 MPa or greater. None limiting examples of such implantable polymers are high density polyethylene (HOPE), ultra-high-molecular-weight polyethylene (UHMWPE), polyether ether ketone (PEEK), carbon-fibre reinforced polyether ether ketone (CFR-PEEK), other polyaryletherketones (PAEK), other carbon-fibre reinforced polyaryletherketones (CFR-PAEK) or higher modulus polyurethanes (e.g. Shore Hardness 75 D and upwards). Other medical grade materials, such as carbon fibre and nylon, may also be used. The clips 9 may also be made from other robust materials, including metals such as steel. Depending on the materials used for the fibres the clip 3 may attach to the fibres mechanically, in any appropriate way, such as looping, via moulding or dip casting.

The bearing 1 may be configured such that the reinforcing element 5 provides additional support for the body 3 of the bearing 1. As the reinforcing member is typically intrinsically linked to the attachment member 7 (where the attachment member 7 is used to hold the bearing 1 in the correct position relative to the remainder of the joint), the remainder of the body 3 of the bearing 1 can be constructed so as to focus on allowing the best possible connection to be formed between the femur and tibia (or prosthetic) surfaces. For example, the body 3 of the bearing 1 can be entirely or partially formed from a low elastic modulus material that can deform under load to conform to the femoral or tibial surface. An embodiment involves an anatomic femoral design. With increasing flexion the sagittal plane radius of an anatomic femoral component decreases. Full congruity in all portions is achieved either by increasing the coronal/transverse plane radius in flexion or by having the centre of curvature in flexion further in the medial direction than in extension.

In addition to having an anatomical femoral component the bearing 1 may be configured to provide an anatomical tibial component which is also poly-radial and poly-centric. The invention therefore allows a bearing 1 to be used which is both anatomically fitted (so as to closely match the natural body components) and is also capable of maintaining congruency with the remaining components of the joint throughout the natural range of movement of the joint. This allows for prosthetic joints which are durable and which allow the user a natural range of movement. The joints are suitable for use by younger, more active patients as they are resistant to wear and the reinforcing member in conjunction with the attachment member 7 means that the bearings are resistant to being dislodged (e.g., by extreme impact loading).

In a further embodiment of the invention, a bearing 101 may be formed at least partially from a polymeric or composite material, and may comprise a lower modulus portion 105 and a higher modulus portion 103, where in one of the modulus portions is at least partially encased within the other modulus portion.

Figure 4:
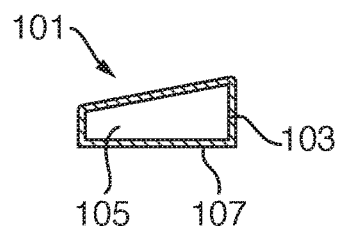
FIG. 4 is a cross section of an embodiment of the bearing.

In some embodiments the lower modulus portion 105 and higher modulus portion 103 of the bearing 101 are both portions within the body 107 of the bearing. Typically, the lower modulus portion 105 of the body 107 is encased within the higher modulus portion 103 of the body 107 (as shown in FIG. 4, which is a cross section of a bearing 101), such that the higher modulus portion 103 of the body 107 can provide support for the lower modulus portion 105 of the body 107. Alternatively, the lower modulus portion 105 can at least partially encase the higher modulus portion 103, such that the higher modulus portion 103 provides a supporting core for the lower modulus portion 105, and the lower modulus portion 105 provides a cushioning layer on the higher modulus portion 103.

The higher modulus portion 103 can be formed from the same compound as the lower modulus portion 105, wherein the lower modulus portion 105 is prepared in such a way as to have a lower modulus than the higher modulus portion 103. Alternatively, the lower and higher modulus portions can be formed from different compounds.

Figure 5:
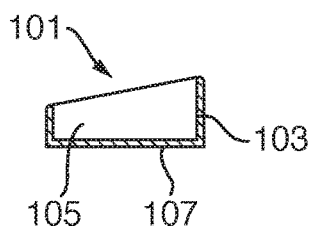
FIG. 5 is a cross section of a further embodiment of the bearing.

In some examples of the bearing 101, the higher modulus portion 103 of the bearing 101 can form a tray-like structure in which the lower modulus portion 105 is configured to sit. This is illustrated in FIG. 5. The higher modulus portion 103 therefore provides additional bracing and support for the lower modulus portion 105. The tray-like structure may take any suitable shape, such as an annular or annular section shape (for example, a horseshoe shape), or an oval shape. In the event that the tray takes an annular or annular section shape, the higher modulus section may provide bracing around all of the surfaces of the bearing 101, or only around some of the surfaces. For example, the higher modulus section may provide bracing around the base and sides of the bearing 101 but not around the top section, or may provide bracing only around the sides of the bearing 101.

The bearing 101 may also be formed from various sections of varying moduli. In particular, the bearing 101 may be constructed with concentric layers of varying moduli. The moduli of the layers may decrease from the edge of the bearing 101 to the centre in the horizontal plane or the sagittal plane or increase from the edge to the centre, or alternate between lower and higher moduli from the edge to the centre.

Where the bearing 101 is formed from portions having different moduli, this allows for a bearing 101 which is more anatomically correct while simultaneously remaining congruent with the femur and tibia (or prosthetic) surfaces. For example, the central portion of the body 107 of the bearing 101 can be formed from a low elastic modulus material that can deform under load to conform to the femoral (and tibial) surface. The exterior portion of the bearing 101 can then provide reinforcement to the remainder of the bearing 101, effectively holding the mere malleable central portion in position. Alternatively, a higher modulus central portion can be used to provide support for a lower modulus outer portion, which is thereby able to be configured so as to deform with the movement of the joint.

An embodiment involves an anatomic femoral design. With increasing flexion the sagittal plane radius of an anatomic femoral component decreases. Full congruity in ail portions is achieved either by increasing the coronal/transverse plane radius in flexion or by having the centre of curvature in flexion further medial than in extension. In addition to having an anatomical femoral component it will be possible to have an anatomical tibial component which is also poly-radial and poly-centric. The invention therefore allows a bearing 101 which is both anatomically fitted (so as to closely match the natural body components) and is also capable of maintaining congruency with the remaining components of the joint throughout the natural range of movement of the joint. This allows for prosthetic joints which are durable and which allow the user a natural range of movement. The joints are suitable for use by younger, more active patients as they are resistant to wear and the reinforcing member in conjunction with the attachment member 7 means that the bearings 101 are resistant to being dislodged (e.g., by extreme impact loading).

The embodiments described above can be combined, such that the features of the embodiments interact synergistically to produce an improved bearing 1,101. For example, a bearing 1,101 may have reinforcing elements 5, an attachment member 7 or members 7, a lower modulus portion 105 and a higher modulus portion 103. The use of both reinforcing elements 5 which encase or permeate the body 3,107 of the bearing 1,101 in conjunction with a higher modulus portion 103 provides additional support for the lower modulus portion 105 of the bearing 1,101, which can therefore be configured to provide the best possible cushioning for the joint without undue concern for the support role of the bearing 1,101. A bearing 1,101 which combines the reinforcing element 5, attachment member 7 or members 7, a lower modulus portion 105 and a higher modulus portion 103 can therefore provide excellent cushioning and fit within a joint.

Several methods may be used to construct the bearing 1,101. The body 3,107 of the bearing 1,101 may be formed by first moulding (for example, injection moulding) the most central layer, typically from a thermosetting polymer as discussed. The further portions of the body 3,107 may then be over-moulded until the desired body 3,107 structure is formed. Bearings 1,101 having a concentric structure may also be formed using dip-coating, wherein an inner portion is formed (for example, by being moulded from a thermosetting polymer) and then outer portions are formed by dip casting onto the inner portion. Particularly good bonds between the layers may be formed if the materials used for the body 3,107 are polymers.

Alternatively or additionally, inner portions of bearings 1,101 having a concentrically layered structure, or entire bearing 1,101 bodies having a uniform material structure, may be formed: using reaction injection moulding (RIM) or structural reaction injection moulding (SRIM), RIM and SRIM can produce a high density, high stiffness outer portion with a lower density inner portion. The inner portion may or may not be filled with a polyurethane material of different hardness to the outer portion. If SRIM is used, the materials used for the reinforcing elements (5) may also serve as the structural element for the SRIM moulded portion.

For hearings 1,101 using reinforcing elements, typically the body 3,107 of the bearing 1,101 will be formed around pre-positioned reinforcing elements. That is, the reinforcing elements 5 are positioned in the mould, and then at least a portion of the body 3,107 of the bearing 1,101 is formed around the reinforcing elements. If further body 3,107 portions are to be added, these can then be moulded onto the body 3,107 portion having the reinforcing elements 5 attached. Alternatively, if the reinforcing elements 5 are to partially or substantially encase the bearing body 3,107, the reinforcing elements 5 can be added after the bearing body 3,107 has been formed, or while the outer portions of the bearing body 3,107 are being formed.

Further construction alternatives involve inserting reinforcing elements 5 through semi-solid body 3,107 portions while the body 3,107 portions are setting, such that the body 3,107 portions ultimately set around the reinforcing elements. A further construction method involves forming the body 3,107 of the bearing 1,101, and then drilling or engraving channels into which the reinforcing elements 5 are subsequently inserted or formed.

The invention claimed is:

1. A bearing for a total or partial joint replacement prosthesis, comprising:
   a body including a lower modulus portion and a higher modulus portion, the higher modulus portion forming a tray structure that receives the lower modulus portion and provides bracing around a bottom surface and two side surfaces of the body; and
   a reinforcing element which strengthens the bearing and which forms an attachment member, wherein the reinforcing element is partially within the body and extends out of the body to form the attachment member, and wherein the attachment member is configured to be attached to a total or partial joint replacement prosthesis.

2. The bearing as claimed in claim 1, wherein the reinforcing element comprises a fibre.

3. The bearing as claimed in claim 1, wherein the reinforcing element comprises a plurality of fibres.

4. The bearing as claimed in claim 3, wherein the fibres are woven together to form the attachment member.

5. The bearing as claimed in claim 3, wherein the fibres are moulded or adhered together to form the attachment member.

6. The bearing as claimed in claim 1, wherein the attachment member comprises a loop.

7. The bearing as claimed in claim 1, wherein the attachment member is configured to be attached to a clip.

8. The bearing as claimed in claim 1, wherein the attachment member is configured to be attached to bone or soft tissue.

9. The bearing as claimed in claim 1, wherein the bearing comprises a plurality of attachment members.

10. The bearing as claimed in claim 2, wherein the fibre forms a mesh which permeates the body.

11. The bearing as claimed in claim 1, wherein the joint replacement prosthesis is a knee joint replacement prosthesis and the attachment member is adapted for attachment to a tibial wall.

12. The bearing as claimed in claim 1, the body being formed at least partially from polymeric or composite material.

13. The bearing as claimed in claim 12, wherein the polymeric or composite material comprises low modulus polyurethane, polycarbonate urethane, hydrogel, hydrogel reinforced with circumferential fibres, high density polyethylene, ultra-high-molecular weight polyethylene, polyether ether ketone, carbon-fibre reinforced polyether ether ketone, other polyaryletherketones, other carbon-fibre reinforced polyaryletherketones or higher modulus polyurethanes.

14. The bearing as claimed in claim 12, wherein the lower modulus portion is formed integrally with the higher modulus portion.

15. The bearing as claimed in claim 12, wherein the lower modulus portion comprises a core portion of the body and the higher modulus portion comprises an outer portion of the body.

16. The bearing as claimed in claim 13, wherein the reinforcing element extends through the lower modulus portion and the higher modulus portion.

17. The bearing as claimed in claim 1, wherein the tray structure provides bracing around an entirety of the body.

18. A bearing and prosthesis system for a total or partial joint replacement, comprising:
   a bearing including:
      a body; and
      a reinforcing element which strengthens the bearing and which forms an attachment member, wherein the attachment member is configured to be attached to a total or partial joint replacement prosthesis; and
   a joint replacement prosthesis including:
      a ibial tray defining a bearing surface that is sized and shaped to receive the body of the bearing; and
      a clip attachable to the ibial tray to secure the attachment member of the bearing to the prosthesis.

19. A bearing for a total or partial joint replacement prosthesis, comprising:
   an annular-shaped body including a first arm and a second arm; and a reinforcing element which strengthens the bearing and which forms an attachment member configured to be attached to a total or partial joint replacement prosthesis, wherein the attachment member includes a first portion protruding from the first arm of the body and a second portion protruding from the second arm of the body, and wherein the first and second portions of the attachment member are linked at a location exterior to the body and near a midline of the body to form a loop.

* * * * *

UNITED STATES PATENT AND TRADEMARK OFFICE
CERTIFICATE OF CORRECTION

PATENT NO. : 10,130,482 B2  
APPLICATION NO. : 15/116447  
DATED : November 20, 2018  
INVENTOR(S) : Khan et al.

Page 1 of 1

It is certified that error appears in the above-identified patent and that said Letters Patent is hereby corrected as shown below:

On the Title Page

In item (71), in "Applicant", in Column 1, Line 1, after "Bridgend", insert --, South Glamorgan--

In item (73), in "Assignee", in Column 1, Line 1, delete "Smith" and insert --, South-- therefor In item (57), in "Abstract", in Column 2, Line 9, before "of", delete "for"

In item (57), in "Abstract", in Column 2, Line 10, delete "hearing." and insert --bearing.-- therefor In the Claims In Column 10, Line 35, in Claim 13, delete "ultra-high-molecular weight" and insert --ultra-high-molecular-weight-- therefor In Column 10, Line 60, in Claim 18, delete "ibial" and insert --tibial-- therefor In Column 10, Line 62, in Claim 18, delete "ibial" and insert --tibial-- therefor Signed and Sealed this  
Second Day of April, 2019

Andrei Iancu  
*Director of the United States Patent and Trademark Office*